(12) United States Patent
Fan et al.

(10) Patent No.: US 10,420,679 B2
(45) Date of Patent: Sep. 24, 2019

(54) HEATED MIST EARACHE AND INFECTION TREATMENT DEVICE

(71) Applicants: Victoria Fan, Stanford, CA (US); Russell D. Fernald, Stanford, CA (US)

(72) Inventors: Victoria Fan, Stanford, CA (US); Russell D. Fernald, Stanford, CA (US)

(*) Notice: Subject to any disclaimer, the term of this patent is extended or adjusted under 35 U.S.C. 154(b) by 104 days.

(21) Appl. No.: 15/493,136

(22) Filed: Apr. 21, 2017

(65) Prior Publication Data

US 2018/0303672 A1 Oct. 25, 2018

(51) Int. Cl.
*A61F 11/00* (2006.01)
*A61M 11/00* (2006.01)
(Continued)

(52) U.S. Cl.
CPC .............. *A61F 11/00* (2013.01); *A61B 1/227* (2013.01); *A61B 90/361* (2016.02); *A61M 3/02* (2013.01);
(Continued)

(58) Field of Classification Search
CPC ...... A61F 2250/0067; A61F 2250/0068; A61F 2/0077; A61F 11/00; A61B 1/227; A61B 2017/00084; A61B 5/03; A61B 5/126; A61B 5/4848; A61B 90/361; A61N 2007/0043; A61N 7/00; A61N 2005/0605; A61N 2005/0661; A61N 5/0603; A61N 5/0624; A61M 2210/0662; A61M 15/0085; A61M 2021/0066; A61M 2021/0072; A61M 2205/36; A61M 2205/50; A61M 31/00; A61M 2205/3368; A61M 11/005; A61M 11/06; A61M 2205/3375; A61M 2205/3653; A61M 2205/52;
(Continued)

(56) References Cited

U.S. PATENT DOCUMENTS

2003/0042772 A1* 3/2003 Park ................... A61B 1/00048
297/217.1
2007/0055200 A1* 3/2007 Gilbert .................... A61M 5/30
604/70

(Continued)

*Primary Examiner* — Brandy S Lee
(74) *Attorney, Agent, or Firm* — The Keith Miller Law Group; Keith Miller

(57) ABSTRACT

The system of the preferred embodiments is an ear treatment device including: an electrical power supply; an electric heater coupled in electronic communication to the electrical power supply; a spray nozzle coupled to a fluid passageway; a fluid reservoir coupled to the opposite end of the fluid passageway from the spray nozzle; at least one of I) a pump, II) an ultrasonic mist generator, and III) a vapor generator designed to cause the fluid from the reservoir to flow through the fluid passageway and out of the spray nozzle; wherein the electric heater is adapted to heat the fluid in at least one of A) the reservoir, B) the fluid passageway, and C) the spray nozzle; wherein the nozzle is adapted to spray the fluid into the ear canal of a user. Preferably the ear treatment device of the preferred embodiments is designed to treat earaches in a user, and possibly to assist in the promotion of drainage of fluid from a user's middle ear and in some cases to treat ear infections. The system of the preferred embodiments may, however, be used for any suitable purpose.

14 Claims, 2 Drawing Sheets

(51) Int. Cl.
*A61B 90/00* (2016.01)
*A61M 11/06* (2006.01)
*A61M 3/02* (2006.01)
*A61B 1/227* (2006.01)
*A61N 5/06* (2006.01)
*G06F 19/00* (2018.01)
*A61B 5/03* (2006.01)
*A61B 5/00* (2006.01)
*A61B 5/12* (2006.01)

(52) U.S. Cl.
CPC ........... *A61M 11/005* (2013.01); *A61M 11/06* (2013.01); *A61B 5/03* (2013.01); *A61B 5/126* (2013.01); *A61B 5/4848* (2013.01); *A61M 2205/3368* (2013.01); *A61M 2205/3375* (2013.01); *A61M 2205/3653* (2013.01); *A61M 2205/52* (2013.01); *A61M 2205/8206* (2013.01); *A61M 2210/0662* (2013.01); *A61N 5/0603* (2013.01); *A61N 5/0624* (2013.01); *A61N 2005/0605* (2013.01); *A61N 2005/0661* (2013.01); *G06F 19/321* (2013.01); *G06F 19/3481* (2013.01)

(58) Field of Classification Search
CPC ............. A61M 2205/8206; A61M 3/02; G06F 19/321; G06F 19/3481
See application file for complete search history.

(56) References Cited

U.S. PATENT DOCUMENTS

2009/0113238 A1* 4/2009 Liu ........................... G06F 1/28
714/14
2015/0065803 A1* 3/2015 Douglas ............. A61B 1/00009
600/200
2016/0317208 A1* 11/2016 Slatkine ................. A61B 18/08
2016/0354559 A1* 12/2016 Gavini .................... A61M 5/30

* cited by examiner

HEATED MIST EARACHE AND INFECTION TREATMENT DEVICE

DESCRIPTION OF THE PREFERRED EMBODIMENTS

This description of the invention is designed to enable someone with skill in the prior art to make and use the invention, however it also does not limit the invention to these embodiments.

Figure 1:
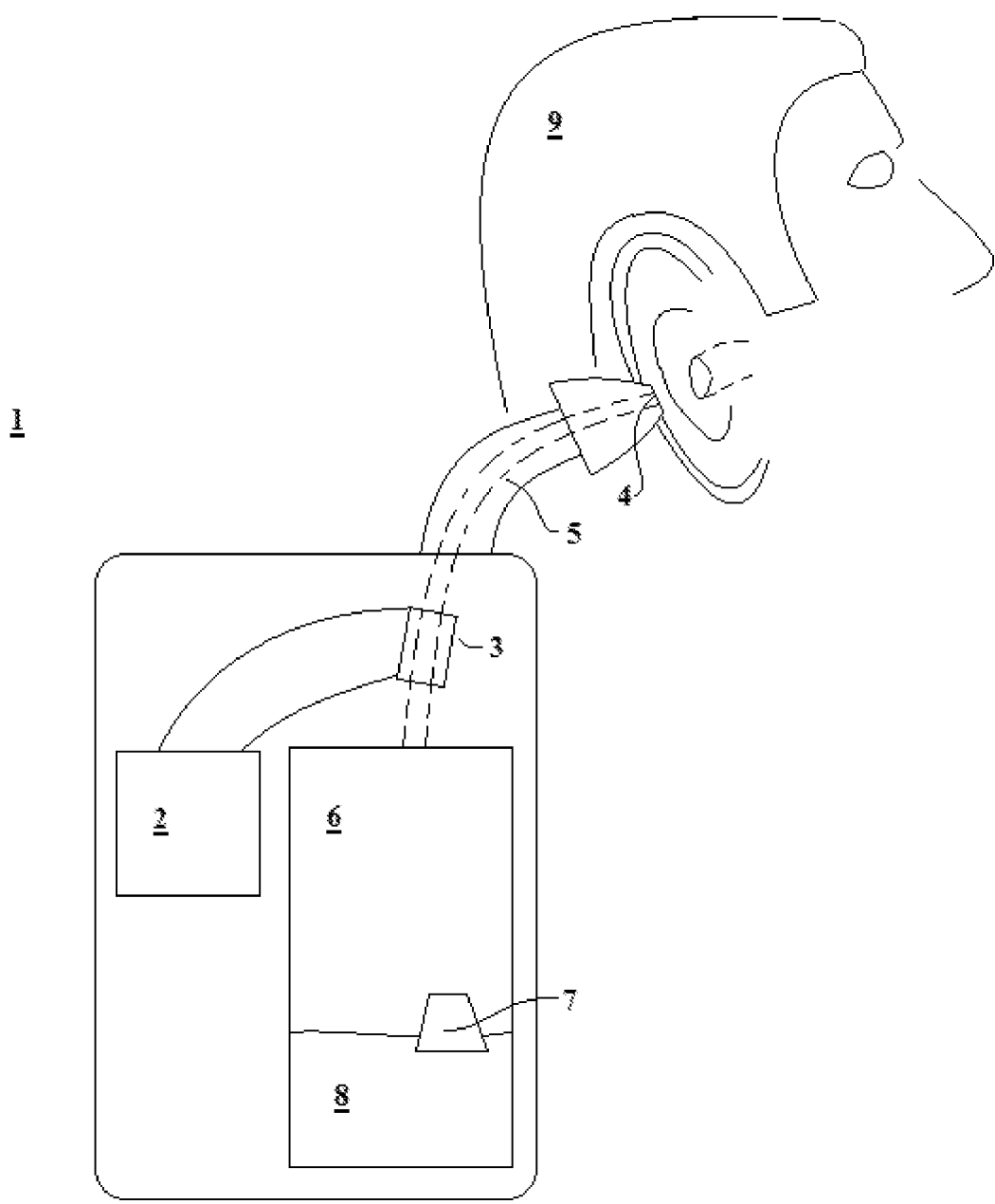
FIG. 1 is a schematic representation of the system of the first preferred embodiments.

As shown in FIG. 1, the system of the preferred embodiments is an ear treatment device 1 including: an electrical power supply 2; an electric heater 3 coupled in electronic communication to the electrical power supply 2; a spray nozzle 4 coupled to a fluid passageway 5; a fluid reservoir 6 coupled to the opposite end of the fluid passageway 5 from the spray nozzle 4; at least one of I) a pump 7, II) an ultrasonic mist generator 7, and III) a vapor generator 7 designed to cause the fluid 8 from the reservoir 6 to flow through the fluid passageway 5 and out of the spray nozzle 4; wherein the electric heater 3 is adapted to heat the fluid 8 in at least one of A) the reservoir 6, B) the fluid passageway 5, and C) the spray nozzle 4; wherein the nozzle is adapted to spray the fluid 8 into the ear canal 21 of a user. Preferably the ear treatment device 1 of the preferred embodiments is designed to treat earaches in a user, and possibly to assist in the promotion of drainage of fluid from a user's middle ear and in some cases to treat ear infections. The system of the preferred embodiments may, however, be used for any suitable purpose.

As shown in FIG. 1, the ear treatment device 1 includes an electrical power supply 2 and an electric heater 3 coupled in electrical communication with the electrical power supply 2. In one preferred variation the electrical power supply 2 is a rechargeable battery. In a variation of this variation, the battery is a lithium polymer battery. In another preferred variation, the power supply is a AC to DC converter that is adapted to supply electrical power from a plug interface with a wall outlet. In another preferred variation, the power supply is a solar panel. There may, however, be any suitable power supply for powering the device. The electric heater 3 may be attached to at least one of the spray nozzle 4, the fluid passageway 5, and the fluid reservoir 6. The electric heater 3 is designed to heat at least one of the fluid 8 and a mist 12 created from the fluid 8 in order to deliver at least one of a heated mist 12 and a heated spray 12 to at least one of the ear canal 21 and the outer ear of the user. In one preferred variation the fluid 8 can be medicated to treat at least one of pain, swelling, and infection. In another preferred variation, the fluid 8 may not be medicated. The at least one of a heated mist 12 and a heated spray 12 preferably provides pain relief and encouragement for the drainage of fluids from the user's middle ear. The at least one of a heated mist 12 and a heated spray 12 may, however, serve any suitable purpose.

As shown in FIG. 1, the ear treatment device 1 includes a spray nozzle 4 attached to one end of a fluid passageway 5, while the opposite end of the fluid passageway 5 is attached to a fluid reservoir 6. In one preferred variation, a mist 12 travels through the fluid passageway 5 and is directed by the spray nozzle 4 into the ear of the user. In another preferred variation, a liquid travels from the fluid reservoir 6 and the spray nozzle 4 causes the liquid to be ejected as a spray 12, and the spray 12 can then be directed into the ear of the user. In another variation, a vapor may be created by a vapor generator 7 and directed through the fluid passageway 5 and out of the spray nozzle 4. The spray nozzle 4 may, however, have any suitable design and use.

As shown in FIG. 1, the ear treatment device 1 includes at least one of a pump 7, an ultrasonic mist generator 7, and a vapor generator 7 designed to cause the fluid 8 from the reservoir 6 to flow through the fluid passageway 5 and out of the spray nozzle 4. In one variation, an electrically driven pump 7 may be included. In another variation, a pump 7 powered by the mechanical force input of the user 9 may be included. In another preferred variation, an ultrasonic mist generator 7 may be included, where the mist generator 7 is in fluid contact with the fluid 8 in the fluid reservoir 6. In another variation, a vapor generator 7 may be included in contact with the fluid 8 in the fluid reservoir 6. There may, however, be any suitable way to cause the fluid 8 to flow through the fluid passageway 5 and out of the spray nozzle 4.

Figure 2:
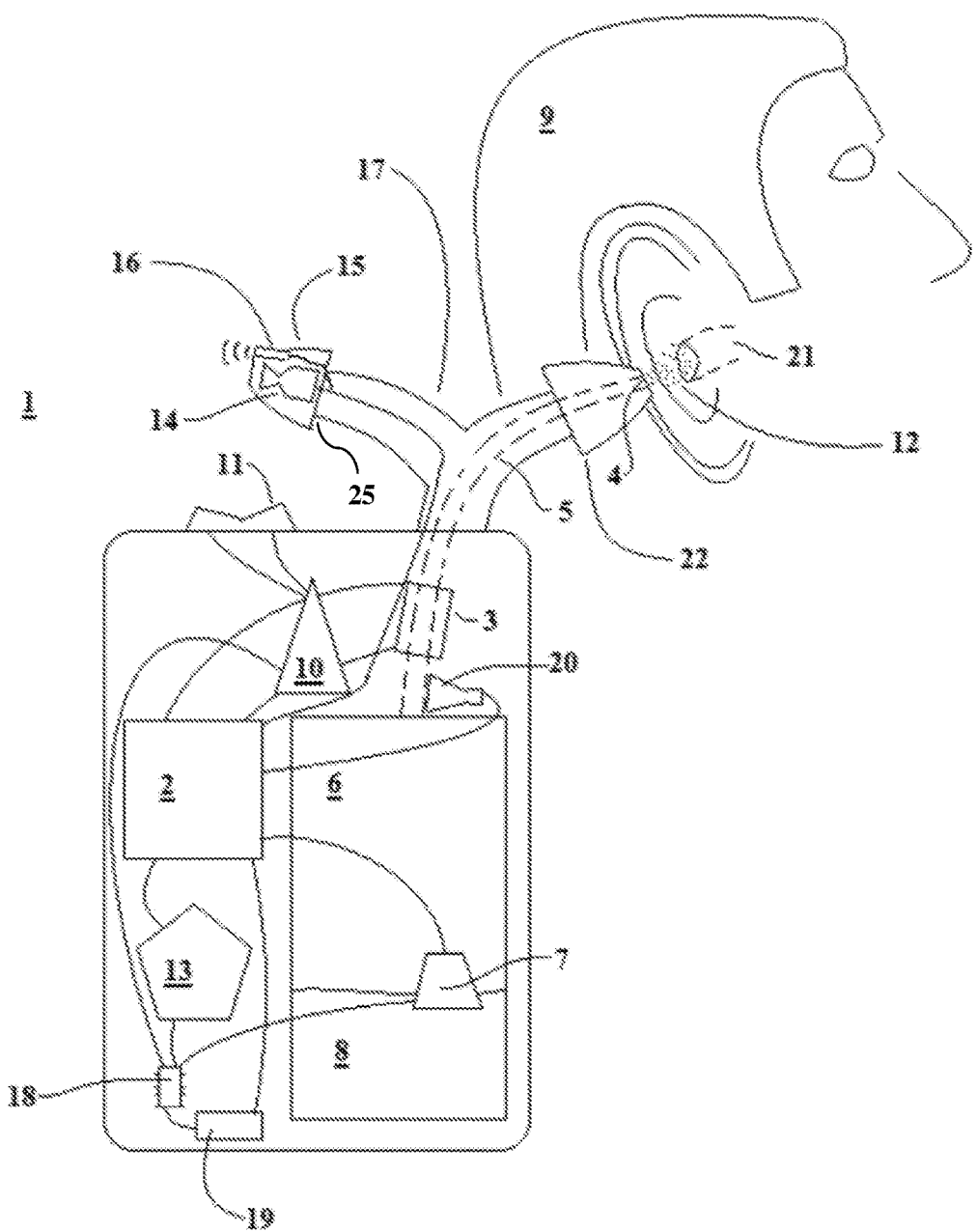
FIG. 2 is a schematic representation of the system of the first preferred embodiments, further including a camera, temperature controller, user interface and other variations of components.

As shown in FIG. 2, in one preferred variation a temperature controller 10 is included that is in electrical communication with the electrical power supply 2, and in electrical communication with the electric heater 3. In this variation, the temperature controller 10 is designed to vary the electrical power delivered from the electrical power supply 2 to the electric heater 3. In this variation, this allows the heat output of the electric heater 3 to be varied. In this variation, there is also a user 9 interface coupled in communication to the temperature controller 10 and designed to allow the user 9 to vary the temperature of the mist 12 by controlling the heat output of the electric heater 3. In one preferred variation of this variation, the user 9 interface can be a rheostat. In another preferred variation of this variation, the user 9 interface can be a digital readout that allows the user 9 to change the desired temperature of the output of at least one of the spray 12 and the mist 12. The user 9 interface is preferably mounted to the outside of a body, where the body contains most of the rest of the ear treatment device 1. However, there may be any suitable design and construction of the ear treatment device 1. The user 9 interface and temperature controller 10 preferably allow the user 9 to vary the temperature of the at least one of spray 12 and mist 12. In one preferred variation, the temperature of the at least one of spray 12 and mist 12 may be varied from 80 degrees F. to 120 degrees F. There may, also, be any suitable design and component choice for the temperature controller 10 and user 9 interface. There may, however, be no temperature controller 10 or user 9 interface at all.

As shown in FIG. 2, in one preferred variation the system of the preferred embodiments further includes a timer 13 wherein the timer 13 is at least coupled in electrical communication to the power supply. The timer 13 preferably is designed to time at least one of A) the time the ultrasonic mist generator 7 is operated for, B) the time the user 9 is to use the device for during an application, and C) the overall time the user 9 is to use the device for over multiple applications with pauses in between to create a treatment session. In a preferred variation, the timer 13 may also be electrically coupled to the ultrasonic mist generator 7. In another preferred variation, the timer 13 may also be electrically coupled to the heater. In a preferred variation, the timer 13 is designed to control the time of application of the at least one of mist 12 and spray 12 to the user's ear. In another preferred variation, the timer 13 notifies the user 9 when to turn off the device, as the desired treatment time has been reached. In another preferred variation, the timer 13 controls both the time of application of the treatment for a treatment interval, and break periods in between multiple treatments carried out over a total treatment time that is longer than an individual treatment interval. In this last variation, multiple treatment intervals may be used and arranged by the timer 13 in order to create a treatment regimen. The timer 13 may, however, be used for any suitable purpose and may be in communication with any suitable components and for the control of any suitable components. There may, however, be no timer 13 included whatsoever.

As shown in FIG. 2, in a preferred variation a camera 14 is mounted in a convergent head 15 attached to the ear treatment device 1. In this variation, the camera 14 can be used to image the inside of the user's ear canal 21 to aide in determining if there is infection, swelling, and other medical analysis. In a variation of this variation, an LED light or other suitable light source may also be included in the convergent head 15 to help in imaging the inside of the user's ear canal. In this variation, preferably the convergent head 15 is designed to align the camera 14 with the opening of the user's ear canal. There may, however, be any suitable design of the convergent head 15. There may, however, be any suitable design for the camera 14 and camera 14 attachment, and the camera 14 may be used for any suitable purpose. There may, however, be any suitable light source or no light source at all. In one variation, a double-head attachment 17 may be attached to the ear treatment device 1, where the double-head attachment 17 can rotate and includes one convergent head 15 with the spray nozzle 4 for treatment, and a second convergent head 15 with at least the camera 14 for medical analysis. In this variation, the rotating double-head attachment 17 is designed both to allow the angle of the heads to be changed for ease and convenience of use, and to allow either the camera 14 head or the convergent head 15 to be rotated into position to be used on the user's ear. In another variation, there may be a single head only with the spray nozzle 4 and the attachment for the single head may be rotatable to allow it to be used at the optimal angle. There may, however, be any suitable attachment for the camera 14 and the spray nozzle 4. There may, however, be no camera 14 at all. As shown in FIG. 2, in one variation there may be a heated cushion around the spray head to warm the user's outer ear during the use of the device. In a variation of this variation, the heated cushion 22 is attached to the convergent head 15 and receives power from the electrical power supply for a resistance heater in the heated cushion 22. There may, however, be no heated cushion whatsoever.

As shown in FIG. 2, in one preferred variation there may be a tympanometry measurement sensor 16 included in the ear treatment device 1, mounted in a convergent head 15 attached to the ear treatment device 1. In one preferred variation, the tympanometry measurement sensor 16 may be mounted in the same convergent head 15 as the camera 14. In another variation, the tympanometry measurement sensor 16 may be mounted in a separate convergent head 15 from the camera 14. The tympanometry measurement sensor 16 is designed to measure the pressure difference between the user's middle ear and the atmosphere to determine if there is a pressure difference causing pain or indicating a medical condition. In one variation, the tympanometry measurement sensor 16 reflects sound waves off of the user's eardrum and measures the results to determine the pressure difference. In one variation the ultrasonic transducer used to generate mist may also be used to generate ultrasound to conduct the tympanometry measurements, allowing a more compact, cost effective, and efficient design. There may, however, be any suitable means for generating mist and any suitable means for generating sound waves for the tympanometry measurements. There may, however, be no tympanometry measurement at all. In one preferred variation, there may be a port 25 in the body that is designed to allow temporary attachment of interchangeable convergent heads 15. In this variation, the spray head may be released from the port 25 and at least one of a camera head, a tympanometry head, and any other suitable head may be interchanged and attached to the port 25 in its place. There may, however, be any suitable attachment means for the at least one convergent head, and there may not be an interchangeable head design at all.

As shown in FIG. 2, in a preferred variation the ear treatment device 1 further includes a processor 18 electronically coupled in communication to the timer 13, to the heater, and to the ultrasonic mist generator 7; and also including computer-readable non-transitory storage medium coupled in communication to the processors 18; wherein the processor 18 is adapted to log data related to the power settings of the electric heater 3, the timing of the treatment, and measurements taken from the camera 14 and tympanometry. In this variation, images and tympanometry readouts can be logged alongside treatment data that includes the timing, temperature, and treatment cycles used to determine what treatments are and are not effective for the user's medical condition. In one variation, there may be an integrated display screen to display pictures taken by the camera. In one variation of this variation, this may be an LCD display. In another variation of this variation, this may be an LED display. In another variation of this variation, the screen may be in wireless communication with the device, rather than integrated into the device body. There may, however, be any suitable use of the processor 18 and the computer-readable non-transitory medium 19. There may, however, be no processor 18 and no computer-readable non-transitory medium 19 included in the ear treatment device 1 at all.

As shown in FIG. 2, in a preferred variation, the ear treatment device 1 further includes an ultraviolet 20 light coupled to at least one of the fluid passageway 5 and the fluid reservoir 6. In this variation, the ultraviolet 20 light is designed to kill microbes in the fluid 8 to ensure that the at least one of mist 12 and spray 12 is delivered in sterilized form. In this variation, this ensures that no additional infection or medical problems will be caused by the device. There may, however, be any suitable means for sterilization used with the device. There may, however, be no ultraviolet 20 light included in the ear treatment device 1 at all.

The preceding description, claims, and drawings would be known to an individual skilled in the prior art to allow modifications and changes to these embodiments without breaking the scope of this invention as defined by the claims.

We claim:
1. An ear treatment device comprising:
   an electrical power supply;
   an electric heater coupled in electronic communication to the electrical power supply;
   a spray nozzle coupled to a first end of a fluid passageway;
   a fluid reservoir coupled to a second end of the fluid passageway opposite the first end of the fluid passageway;

a mist generating subunit comprising at least one of a pump, an ultrasonic mist generator, and a vapor generator configured to cause a fluid from the fluid reservoir to flow through the second end of the fluid passageway and out of the spray nozzle at the first end of the fluid passageway;

a rotatable attachment coupled to the first end of the fluid passageway, the rotatable attachment comprising two convergent heads, wherein one of the two convergent heads comprises the spray nozzle, and a second of the two convergent heads comprises a camera, and wherein the rotatable attachment is configured to rotate to change an angle of one or more of the two convergent heads and to allow alternating use of the spray nozzle and the camera in the ear canal of the user; wherein the camera mounted in one of the two convergent heads is disposed at the first end of the fluid passageway, wherein the camera is configured to view into the ear canal of the user; and a user interface coupled in electrical communication to the electric heater and configured to allow the user to adjust settings relating to the user's condition, wherein the user interface comprises a display screen, wherein the display screen of the user interface is further configured to display pictures taken by the camera;

wherein the electric heater is configured to heat the fluid in at least one of the reservoir, the fluid passageway, and the spray nozzle; and wherein the spray nozzle is configured to spray the fluid into an ear canal of a user to achieve at least one of pain relief caused by an earache, drainage of accumulated fluid in the user's middle ear, and treatment for pain, swelling, and infection due to an ear infection.

2. The ear treatment device of claim 1, further comprising:
a temperature controller coupled in electrical communication to the electric heater, wherein the temperature controller is configured to vary an electrical power delivered from the electrical power supply to the electric heater; and wherein the user interface is further coupled in electrical communication to the temperature controller and configured to allow the user to vary a heat output of the electric heater.

3. The ear treatment device of claim 2, further comprising a timer coupled in electrical communication to at least the electrical power supply, wherein the timer is configured to time at least one of an amount of time that the mist generating subunit is operated, an amount of time the user operates the ear treatment device during an application, and a treatment session time that the user operates the ear treatment device, wherein the treatment session includes multiple applications with pauses in between the multiple applications.

4. The ear treatment device of claim 2, further comprising an ultraviolet light adapted to expose the fluid in at least one of the fluid reservoir and the fluid passageway to ultraviolet light in order to sterilize the fluid, and coupled to at least one of the fluid passageway and the fluid reservoir.

5. The ear treatment device of claim 2, further comprising a heated cushion disposed around the spray nozzle and configured to warm an outer ear of the user during use of the ear treatment device, wherein the heated cushion comprises a resistance heater configured to receive power from the electrical power supply, wherein the temperature controller is further configured to vary an electrical power delivered from the electrical power supply to the heated cushion, and wherein the user interface is configured to allow the user to vary the heat output of the heated cushion.

6. The ear treatment device of claim 3, further comprising a tympanometry measurement sensor mounted to at least one of the first head or a second convergent head and configured to measure a pressure difference between a middle ear of the user and an atmospheric pressure, wherein the at least one of the first convergent head or the second convergent head is attached to the ear treatment device.

7. The ear treatment device of claim 3, further comprising a port disposed at the first end of the fluid passageway, the port configured to allow temporary attachment of interchangeable convergent heads.

8. The ear treatment device of claim 6, further comprising a processor electronically coupled in communication to the timer, to the heater, and to the ultrasonic mist generator; and also comprising computer-readable non-transitory storage medium coupled in communication to the processors; wherein the processor is adapted to log data related to the power settings of the electric heater, the timing of the treatment, and measurements taken from the camera and tympanometry.

9. The ear treatment device of claim 6, further comprising a processor electronically coupled in communication to the timer, to the heater, and to the ultrasonic mist generator; and also comprising computer-readable non-transitory storage medium coupled in communication to the processors; wherein the processor is adapted to log data related to the power settings of the electric heater, the timing of the treatment, and measurements taken from the camera and tympanometry.

10. The ear treatment device of claim 6, further comprising a port disposed at the first end of the fluid passageway, the port configured to allow temporary attachment of a number of interchangeable convergent heads, wherein at least one of the first convergent head and the second convergent head is attached to the ear treatment device via the port and is among the number of interchangeable convergent heads.

11. The ear treatment device of claim 6 wherein the rotatable attachment comprising the two convergent heads is coupled to the first end of the fluid passageway via a port configured to allow temporary attachment of a number of interchangeable convergent heads.

12. The ear treatment device of claim 8, further comprising an ultraviolet light adapted to expose the fluid in at least one of the fluid reservoir and the fluid passageway to ultraviolet light in order to sterilize the fluid, and coupled to at least one of the fluid passageway and the fluid reservoir.

13. The ear treatment device of claim 1, further comprising a tympanometry measurement sensor mounted to at least one of the first convergent head or a second convergent head and configured to measure a pressure difference between a middle ear of the user and an atmospheric pressure, wherein the at least one of the first convergent head or the second convergent head is attached to the ear treatment.

14. The ear treatment device of claim 1, further comprising a heated cushion disposed around the spray nozzle and configured to warm an outer ear of the user during use of the ear treatment device, wherein the heated cushion comprises a resistance heater configured to receive power from the electrical power supply.

* * * * *